(12) United States Patent
Saunders et al.

(10) Patent No.: US 11,215,734 B2
(45) Date of Patent: Jan. 4, 2022

(54) GEOLOGICAL SOURCE-TO-SINK ANALYSIS AND DISPLAY SYSTEM

(71) Applicant: Landmark Graphics Corporation, Houston, TX (US)

(72) Inventors: Benjamin Stephen Saunders, Oxfordshire (GB); Graeme Richard Nicoll, Oxfordshire (GB); Graham Baines, Oxfordshire (GB)

(73) Assignee: Landmark Graphics Corporation, Houston, TX (US)

( * ) Notice: Subject to any disclaimer, the term of this patent is extended or adjusted under 35 U.S.C. 154(b) by 406 days.

(21) Appl. No.: 16/083,604

(22) PCT Filed: Mar. 19, 2018

(86) PCT No.: PCT/US2018/023113
§ 371 (c)(1),
(2) Date: Sep. 10, 2018

(87) PCT Pub. No.: WO2019/108245
PCT Pub. Date: Jun. 6, 2019

(65) Prior Publication Data
US 2021/0011192 A1 Jan. 14, 2021

Related U.S. Application Data

(60) Provisional application No. 62/591,948, filed on Nov. 29, 2017.

(51) Int. Cl.
*G01V 99/00* (2009.01)
*G01N 33/24* (2006.01)

(52) U.S. Cl.
CPC ........... *G01V 99/005* (2013.01); *G01N 33/24* (2013.01); *G01V 2210/661* (2013.01); *G01V 2210/665* (2013.01)

(58) Field of Classification Search
CPC ........... G01V 99/005; G01V 2210/661; G01V 2210/665; G01N 33/24
(Continued)

(56) References Cited

U.S. PATENT DOCUMENTS

2009/0319243 A1* 12/2009 Suarez-Rivera ........ G06T 17/05
703/10
2012/0023118 A1 1/2012 Savary-sismondini et al.
(Continued)

FOREIGN PATENT DOCUMENTS

WO 2016130945 8/2016
WO 2016144763 9/2016

OTHER PUBLICATIONS earthref.org Newsletter, "Earth Reference Data and Models: Geochron 1.0 Release", https://earthref.org/newesletter/2011/er-news-01.htm, 2011, 1 page.
(Continued)

*Primary Examiner* — Ricky Go
(74) *Attorney, Agent, or Firm* — Kilpatrick Townsend & Stockton LLP

(57) ABSTRACT

Analysis and display of source-to-sink information according to some aspects includes grouping target geochronological data and reference geochronological data into distinct population groups representing a reference population and target populations and characterizing subpopulations within the reference population and the target populations according a statistical attribute or statistical attributes. Subpopulations are compared within the reference population and the target populations based on the statistical attribute or attributes to determine correlations between the reference population and the target populations, and the results can be displayed in many different ways. As one example, results can be displayed using a present day geographic map as well as using a geodynamic plate tectonic model to show data
(Continued)

points and their paleogeographic locations for the relevant geological time frame of investigation.

20 Claims, 12 Drawing Sheets

(58) Field of Classification Search
USPC .................................................. 702/5
See application file for complete search history.

(56) References Cited

U.S. PATENT DOCUMENTS

| | | | |
|---|---|---|---|
| 2013/0204598 A1 | 8/2013 | Mallet | |
| 2013/0275101 A1 | 10/2013 | Hsu et al. | |
| 2013/0317751 A1 | 11/2013 | Dreyfus et al. | |
| 2013/0317779 A1* | 11/2013 | Thorne | G01V 11/00 702/180 |
| 2014/0330519 A1 | 11/2014 | Mueller | |
| 2015/0159471 A1 | 6/2015 | Jones | |
| 2015/0355353 A1* | 12/2015 | Whitaker | G01V 1/345 702/14 |
| 2016/0018556 A1* | 1/2016 | Montgomery | G01N 33/24 702/2 |
| 2016/0146973 A1* | 5/2016 | Johnson | G01V 99/005 702/2 |
| 2016/0209544 A1 | 7/2016 | Minguez et al. | |
| 2017/0075031 A1 | 3/2017 | Mallet | |
| 2017/0108617 A1* | 4/2017 | Fei | E21B 43/00 |
| 2017/0184760 A1 | 6/2017 | Li et al. | |
| 2017/0337302 A1* | 11/2017 | Mezghani | G06F 30/17 |
| 2019/0145253 A1* | 5/2019 | Spence | E21B 43/26 175/50 |

OTHER PUBLICATIONS

Jasra et al., "Bayesian Mixture Modelling in Geochronology via Markov Chain Monte Carlo", Mathematical Geology, vol. 38, Issue 3, Apr. 2006, pp. 269-300.

Ocean News & Technology, "CGG Launches Provenance, a Global Sediment Provenance Solution (/news/milestones/cgg-launches-provenance-a-global-sediment-provenance-solution)", available at https://www.oceannews.com/news/milestones/cgg-launches-provenance-a-global-sediment-provenance-solution, Apr. 26, 2017, 2 pages.

International Patent Application No. PCT/US2018/023113, International Search Report and Written Opinion dated Aug. 14, 2018, 11 pages.

Saylor et al., "Quantifying comparison of large detrital geochronology data sets", Geosphere, vol. 12(1), 2016, pp. 203-220.

Vermeesch, "Multi-Sample comparison of detrital age distributions", Chemical Geology, vol. 341, Mar. 11, 2013.

* cited by examiner

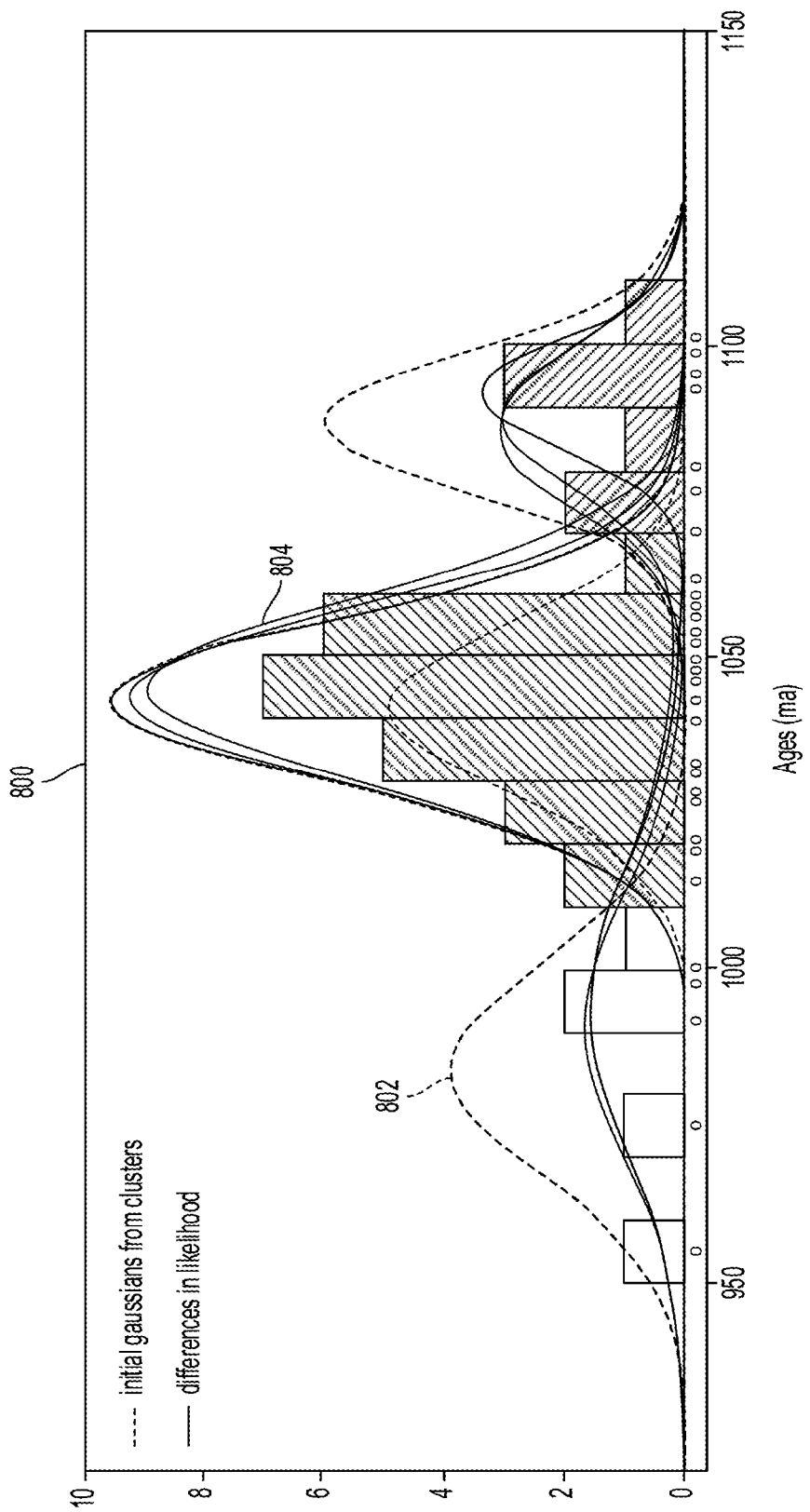

GEOLOGICAL SOURCE-TO-SINK ANALYSIS AND DISPLAY SYSTEM

TECHNICAL FIELD

The present disclosure relates generally to digital processing of geochronological data obtained from geological materials. More specifically this disclosure relates to the processing of source-to-sink information and the interactive display of such information on a paleogeographic map.

BACKGROUND

Source-to-sink analysis is currently an assessment carried out over the course of weeks or months by geoscientists who are seeking to understand risks associated with clastic hydrocarbon reservoirs. The analysis is typically carried out by mapping out the origin of the sediments and their historic drainage networks throughout geological time. The analysis typically involves using many disparate datasets.

In recent years the number of detrital zircon geochronology studies being published has grown exponentially. The detrital geochronology datasets from these studies can be important aids to source-to-sink analysis and clastic reservoir characterization. However, as the quantity of data available increases, traditional data analysis techniques used within regional studies are becoming untenable.

BRIEF DESCRIPTION OF THE DRAWING

FIG. 8 is a graph illustrating the application of expectation-maximization to Gaussian mixture models according to some aspects.

DETAILED DESCRIPTION

Certain aspects of the present disclosure relate to a system and processes that improve, and make more efficient, the analysis and comparison of a multiple statistical populations of geochronological data obtained from geological materials. The processes use statistical methods to quickly identify and characterize subpopulations of data (e.g. detrital zircon single grain ages) from within a larger sample population or group of populations. The system compares distinct populations on the basis of these subpopulations. The terms "population" and "subpopulation" are used herein in the statistical sense. A population is a large group of zircons that can be generalized from a limited number of samples with respect to some property. A subpopulation is a portion of a population where zircons share an additional property. Example properties include age range, geographic location, and time of deposition. The system and processes described herein provide automated, integrated, and rapid provenance investigations, which can be used in natural resource exploration to assess the nature and quality of sedimentary rocks hosting hydrocarbon reservoirs.

Analysis and display of source-to-sink information according to some aspects includes grouping target geochronological data and reference geochronological data into distinct population groups representing a reference population and target populations and characterizing subpopulations within the reference population and the target populations according a statistical attribute or statistical attributes. Subpopulations are compared within the reference population and the target populations based on the statistical attribute or attributes to determine correlations between the reference population and the target populations, and the correlations are concurrently displayed relative to a present day geographic map with links between source regions and sink regions, and relative to a paleogeographic map as of a time of relevance.

Figure 1:
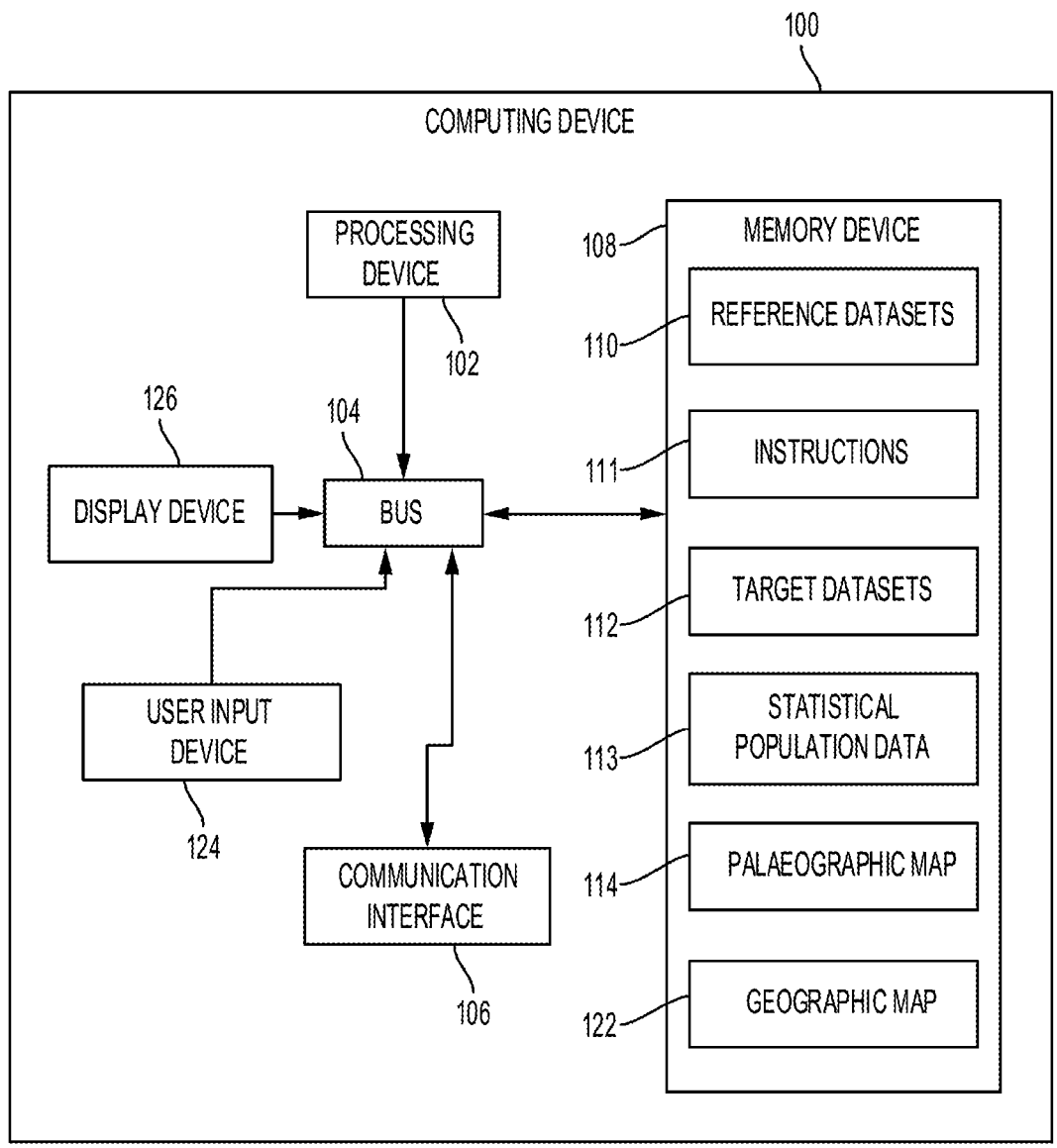
FIG. 1 is a block diagram depicting a computing device for carrying out geological provenance analysis including source-to-sink analysis according to some aspects.

FIG. 1 depicts an example of a computing device 100 according to one example. The computing device 100 can include a processing device 102, a bus 104, a communication interface 106, a non-transitory or non-volatile memory device 108, a user input device 124, and a display device 126. In some examples, some or all of the components shown in FIG. 1 can be integrated into a single structure, such as a single housing. In other examples, some or all of the components shown in FIG. 1 can be distributed (e.g., in separate housings) and in communication with each other.

The processing device 102 can execute one or more operations for providing a source-to-sink analysis. The processing device 102 can execute instructions 111 stored in the memory device 108 that are executable by the processing device 102 to perform the operations. The processing device 102 can include one processing device or multiple processing devices. Non-limiting examples of the processing device 102 include a Field-Programmable Gate Array ("FPGA"), an application-specific integrated circuit ("ASIC"), a microprocessing device, etc.

The processing device 102 can be communicatively coupled to the memory device 108 via the bus 104. The non-volatile memory device 108 may include any type of memory device that retains stored information when powered off. Non-limiting examples of the memory device 108 include electrically erasable and programmable read-only memory ("EEPROM"), flash memory, or any other type of non-volatile memory. In some examples, at least some of the memory device 108 can include a non-transitory medium from which the processing device 102 can read instructions. A non-transitory computer-readable medium can include electronic, optical, magnetic, or other storage devices capable of providing the processing device 102 with computer-readable instructions or other program code. Non-limiting examples of a computer-readable medium include (but are not limited to) magnetic disk(s), memory chip(s), read-only memory (ROM), random-access memory ("RAM"), an ASIC, a configured processing device, optical storage, or any other medium from which a computer processing device can read instructions. The instructions can include processing device-specific instructions generated by a compiler or an interpreter from code written in any suitable computer-programming language, including, for example, C, C++, C#, etc.

In some examples, the memory device 108 can include reference datasets 110, gathered and grouped from a geochronological database or multiple geochronological databases. This data may represent detrital zircon data from a reservoir sample or mineral ages from a specific geographical region. In some examples, the computer program instructions 111 define subpopulations within each data group under investigation, characterize the data by statistical attributes (e.g. mean, variance, proportion of total population, skew, kurtosis, etc.), compare and correlate subpopulations, and carry out the other aspects of the process. The memory device 108 can also include target datasets 112, gathered and grouped from one or more geochronological databases. The memory device 108 can include statistical population data 113, which can include statistical attributes of subpopulations from geochronological data. The memory device 108 can include a stored paleogeographic map 114 and a stored geographic map 122.

In some examples, the computing device 100 includes a communication interface 106. The communication interface 106 can represent one or more components that facilitate a network connection or otherwise facilitate communication between electronic devices. Examples include, but are not limited to, wired interfaces such as Ethernet, USB, IEEE 1394, and/or wireless interfaces such as IEEE 802.11, Bluetooth, near-field communication (NFC) interfaces, RFID interfaces, or radio interfaces for accessing cellular telephone networks (e.g., transceiver/antenna for accessing a CDMA, GSM, UMTS, or other mobile communications network).

In some examples, the computing device 100 includes a user input device 124. The user input device 124 can represent one or more components used to input data. Examples of the user input device 124 can include a keyboard, mouse, touchpad, button, or touch-screen display, etc.

In some examples, the computing device 100 includes a display device 126, which can display the maps described herein and other information used in the process described herein. The display device 126 can represent one or more components used to output data. Examples of the display device 126 can include a liquid-crystal display (LCD), a television, a computer monitor, a touch-screen display, etc. In some examples, the user input device 124 and the display device 126 can be a single device, such as a touch-screen display.

The example techniques described below make use of large globally consistent datasets of geochronology data, for both hinterland and basin areas, which are continually sourced, updated and maintained to allow for enhanced regional predictions. These large datasets are available in a standardized format which allows for direct comparison, statistical calculations and rapid outputs. Detrital zircon ages for sediment samples published in the public domain are extracted and entered into a relational geochronological database. Age data for both hinterland and sink regions is included. Fields containing the age and analytical error of each zircon crystal are used, as is the depositional age of the sedimentary unit the zircon crystal have been extracted from. Once this information is captured and standardized it can be imported for statistical analysis.

Figure 2:
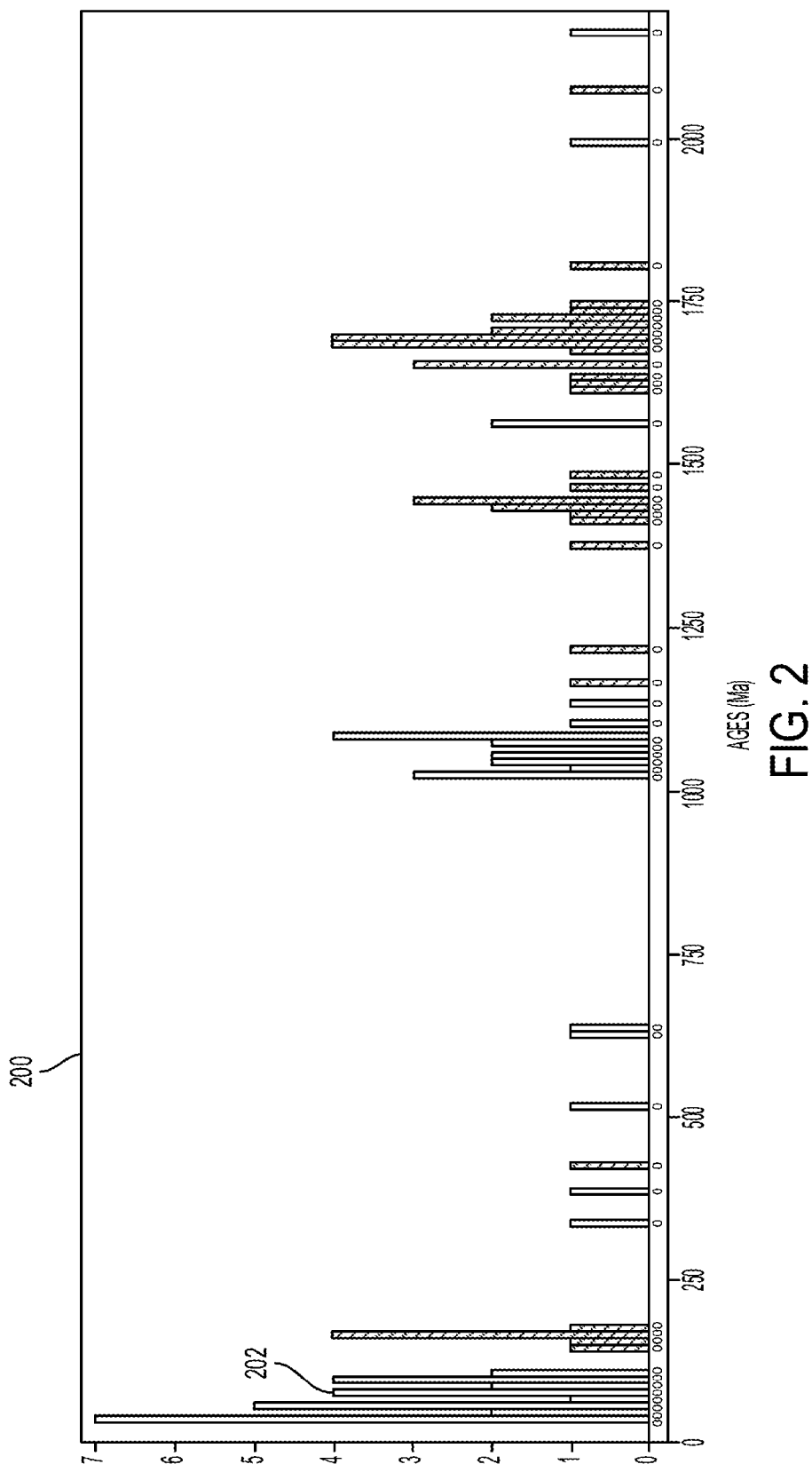
FIG. 2 is a graph illustrating a stage of agglomerative clustering according to some aspects.
Figure 3:
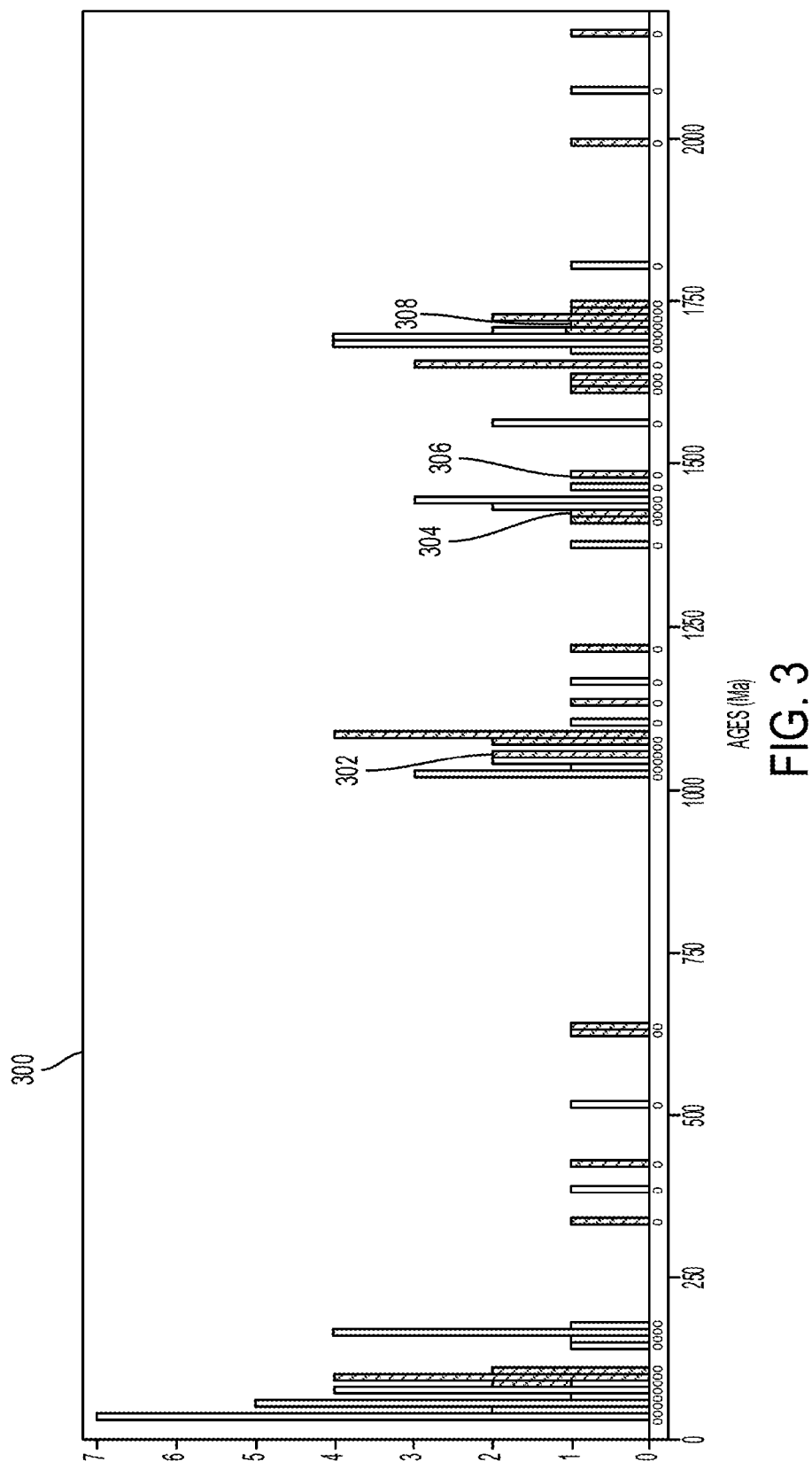
FIG. 3 is a graph illustrating another stage of agglomerative clustering according to some aspects.
Figure 4:
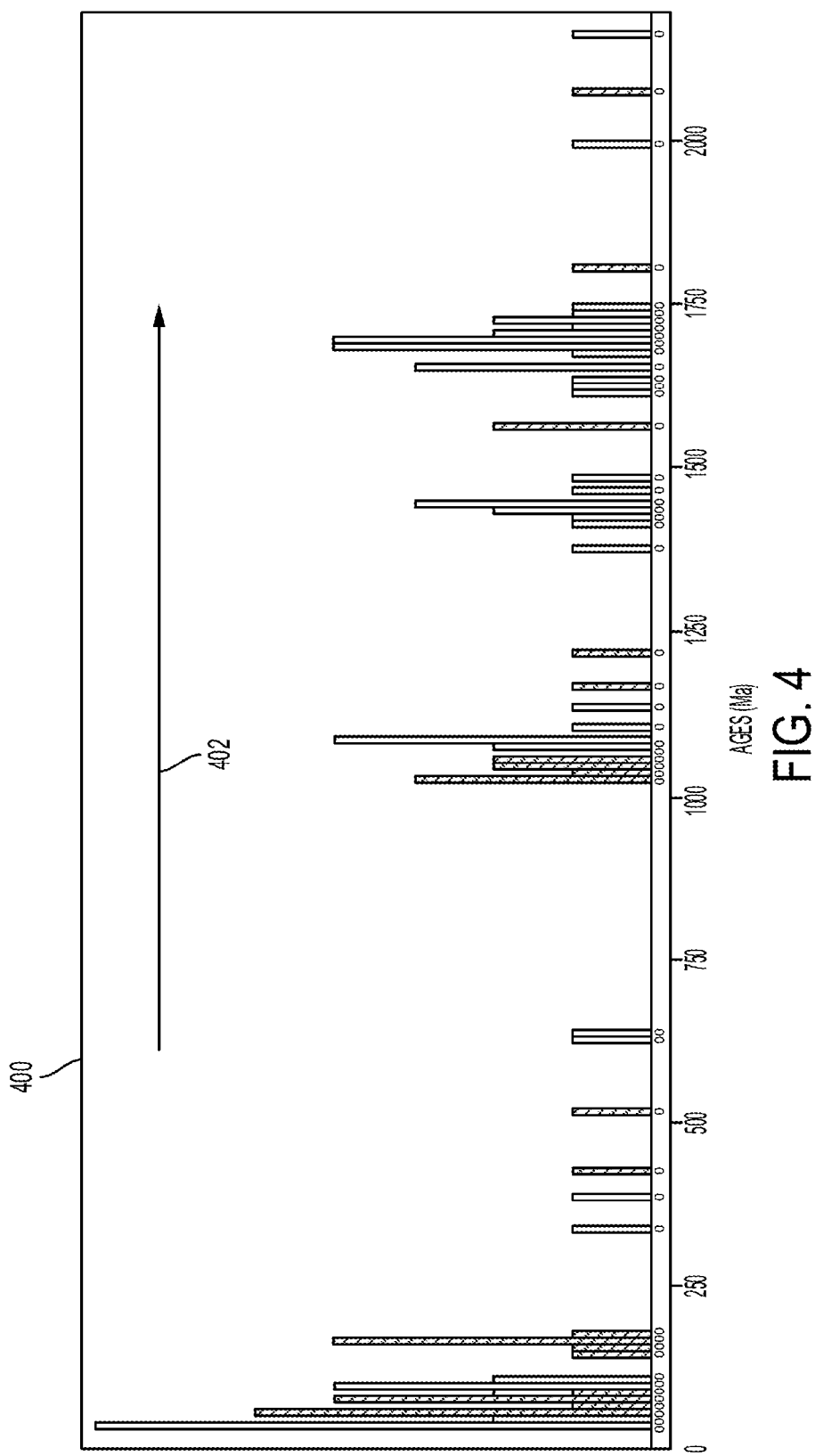
FIG. 4 is a graph illustrating agglomerative clusters according to some aspects.

Agglomerative clustering, as an example, can be used to group initial subpopulations in the zircon age data. Firstly a low k (number of clusters) is used to identify broad subpopulations. The graphs of FIG. 2, FIG. 3, and FIG. 4 illustrate this technique. FIG. 2 shows graph 200 where subpopulation clusters are shown according to age for k=16. In an actual display, the number of apparent subpopulations might be indicated with different colors. For illustration purposes, FIG. 2 enables one to generally see differing clusters by variation in shading or fill. As is shown by the unitary shading of the large clusters 202 below about 200 Ma in age, more clusters are required for younger subpopulations. For the subpopulation clusters shown in graph 300 of FIG. 3, k is increased and the clusters are assessed using the Shapiro score. The solution with the greatest Shapiro score is the most optimized solution and is used to set a value for k. In the case of FIG. 3, k=29. This setting results in an improbable cluster split 302 and over-interpretations 304, 306, and 308 of the number of clusters.

Further sub-clusters are defined based on a set of parameters defined by the user. These parameters are geological rules with values that specify the maximum age range of geological events allowed in a particular cluster. Any clusters with age ranges larger than these geological rule values are broken down by the sub-clustering method. The sub-clustering method involves using agglomerative clustering and k-means clustering to optimize the sub-clusters. A final part of the agglomerative clustering process takes into account the analytical error of each of the zircon ages, joins clusters that are within the analytical error of each other and splits clusters that are outside of each other's analytical error. FIG. 4 shows graph 400, with sub-clusters optimized using this two-step clustering approach. A decreasing number of clusters are assigned as age increases from left to right, as indicated by arrow 402.

Figure 5:
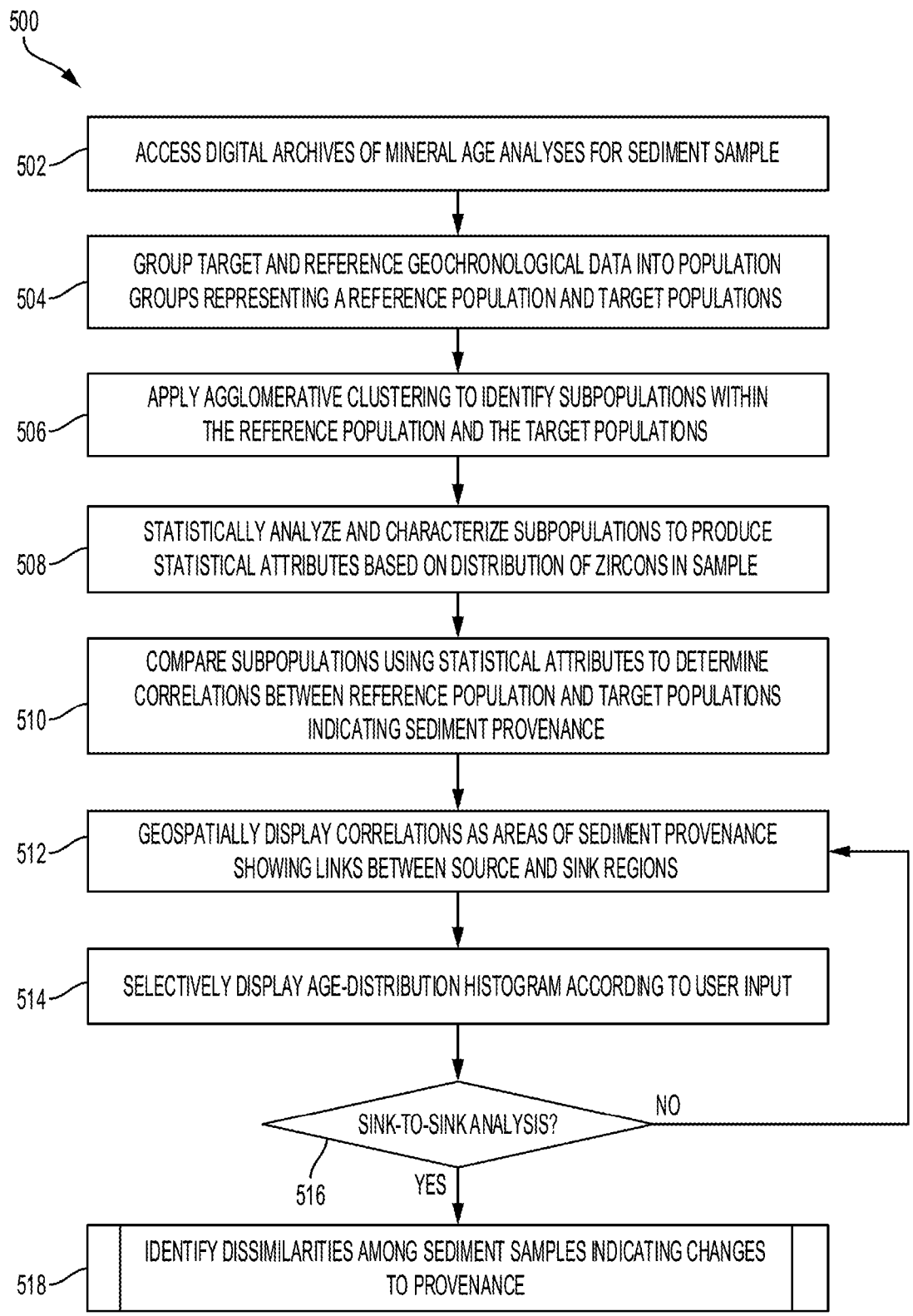
FIG. 5 is a flowchart illustrating a process for source-to-sink analysis and provenance display according to some aspects.

FIG. 5 is a flowchart showing a process 500 for performing a source-to-sink analysis and displaying results including source-to-sink analysis information for a sediment sample. In this example, process 500 is carried out by computing device 100 of FIG. 1. At block 502 digital archives are accessed, for example through communication interface 106 of FIG. 1. The digital archives include data that may represent detrital zircon data from a reservoir sediment sample or mineral ages from a specific geographical region. The selected data may also be limited to a specific geological age range. At block 504, target geochronological data and reference geochronological data are grouped into distinct population groups representing a reference population and target populations. The data is stored as a reference dataset 110 and target datasets 112. At block 506, subpopulations within the reference population and target populations are identified and defined by processing device 102. In some aspects, agglomerative clustering of zircon age data as previously described is used to define subpopulations. At block 508, the subpopulations are statistically analyzed by processing device 102 and characterized to produce a statistical attribute or statistical attributes based on the distribution of zircons in the sample. Such statistical attributes are stored as statistical population data 113 shown in FIG. 1. Statistical attributes can include, as examples, mean, variance, proportion of total population, skew, and kurtosis. In some aspects, the statistical analysis includes defining Gaussian mixture models that reproduce the reference population and the target populations using the subpopulations as a priori constraints. The Gaussian mixture models describe a distribution of zircons in the sediment sample. The details of an example statistical analysis will be further discussed below with respect to FIGS. 8, 9A, and 9B.

Continuing with FIG. 5, at block 510 processing device 102 compares subpopulations using the statistical attribute or attributes to determine correlations between the reference population and target populations. Such correlations can indicate sediment provenance, since they determine the likelihood that each subpopulation from a reference sample is present in the target samples. At block 512, correlations are displayed on display device 126 geospatially as areas of sediment provenance showing links between source and sink regions. Numerous display options and types can be selected and controlled by a user through user input device 124. Some of these options will be discussed in further detail with respect to the remaining figures. As one example, a user can choose at block 514 to have computing device 100 selectively display a distribution histogram of geological age versus frequency of occurrence. As another example, the correlations can be displayed concurrently on a present day geographic map and on a paleogeographic map at a time of relevance. The paleographic map can be based on geodynamic plate tectonic model. A user can also choose at block 516 to have computing device 100 perform a sink-to-sink analysis. If such an analysis is triggered, processing device 102 can, at block 518, calculate and identify dissimilarity values representing differences between the sediment sample and additional samples that may indicate changes in provenance. In some aspects, a dendrogram indicating the dissimilarity values can be displayed. This feature and the process of block 518 will be discussed in further detail with respect to FIGS. 10 and 11.

Figure 6:
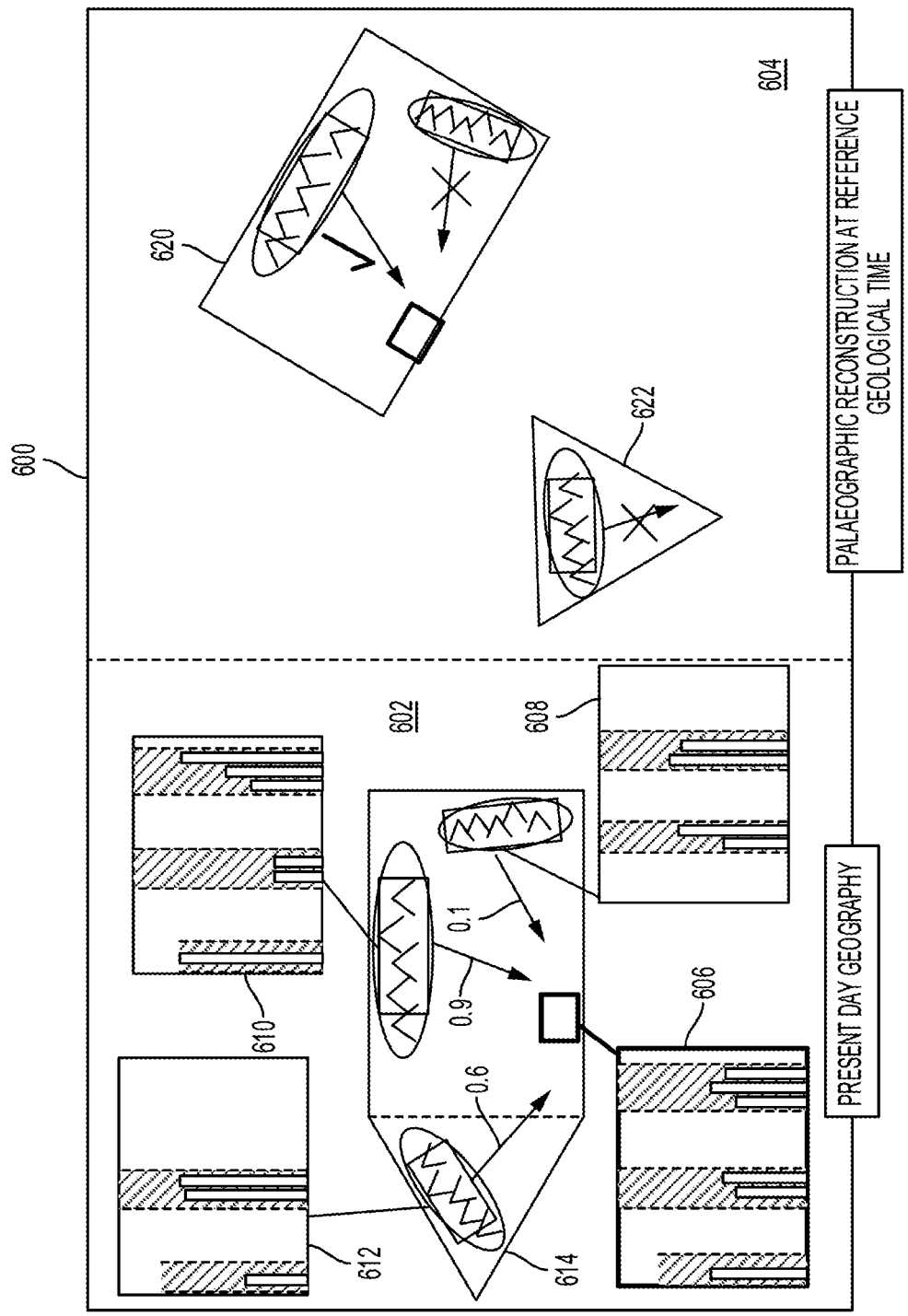
FIG. 6 depicts a graphical display of maps produced according to some aspects.

FIG. 6 depicts a graphical display 600 of maps produced according to some aspects. The maps are presented at a continental scale (100's-1,000's km) on display device 126. Map area 602 includes a present day geographic map with links between source regions and sink regions, and map area 604 includes a paleogeographic map at a time of relevance. Map area 602 can be stored as geographic map 122 of FIG. 1. Map area 602 shows reference geochronological dataset 606, based on, as an example, a sediment sample from a reservoir interval containing detrital zircon geochronology information or a group of detrital geochronology samples from the same formation or time interval. Map area 602 also shows target geochronological datasets 608, 610, and 612, based on, as an example, hard rock geochronology data, grouped by distinct region, relating to the formation or modification of that hinterland region. Subpopulations, of geological age, within each group are calculated and can be displayed as histograms of age versus frequency, which are schematically illustrated in FIG. 6 for each dataset. The subpopulations are then statistically compared and a probability score is calculated, for example, to indicate likely source areas that have been eroded to produce the sediment being investigated, for example, the region corresponding to dataset 606. Each region's dataset is shown with a line indicating the corresponding region on map 614. Arrows indicate links showing potential pathways for linking source regions to sink regions, for example, river systems.

Still referring to FIG. 6, the results are also viewed within a paleographical context in map area 604 to assess the continental plate tectonic configuration at the time of formation for the region corresponding to dataset 606, e.g. 200 million years ago. The paleographic map in this case, stored as paleographic map 114 in FIG. 1, is shown in two portions, portion 620 and portion 622. The display of regions of interest at a reference time provides critical extra insight and can be used to exclude certain target areas from having a connection to the reference area, e.g. the area corresponding to dataset 612 cannot contribute material to the area corresponding to dataset 606 at this particular geological time frame, as shown in map portion 622, and should be ruled out for source-to-sink investigations. The paleographic map portions in map area 604 show that two links can be discounted.

Figure 7:
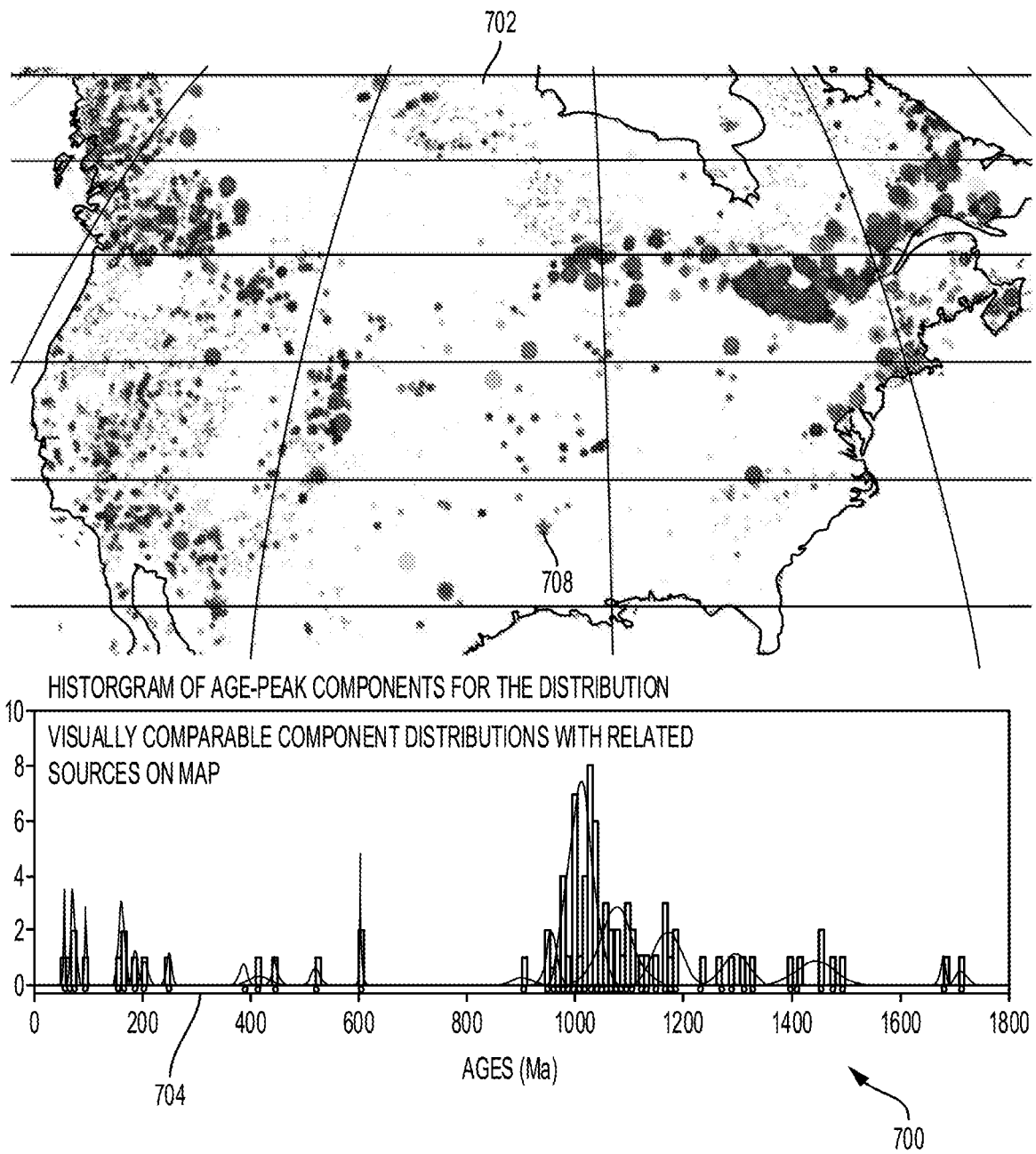
FIG. 7 depicts a graphical display including a map and a histogram produced according to some aspects.

FIG. 7 depicts an interactive graphical display 700 including a map 702 and a histogram 704 produced according to some aspects and displayed on display device 126. In this example, geospatial results are reconstructed on a geodynamic plate model at the age of deposition of a detrital sediment sample and displayed on map 702. This display provides the user with a visualization of the paleogeography at the time of deposition and allows the user to discount sediment source areas that may not have been connected to the sink at the time of deposition. Such a display may highlight previously unknown sediment source areas that are no longer geographically connected to the sink in the present day. The user may selectively display a histogram showing age-peak components for a specific sample. The term "selectively" in this context can have one or both of two meanings, that user selection determines whether or not to display the histogram and also that user selection can determine which sample's histogram is displayed. In either or both cases, an interactive display of data regarding user-visualized geological samples takes place, with the computing device responding to user selections. In this example, the user can click, touch, or "mouse over" a particular sample point on the map with user input device 124 and the age-distribution histogram for that particular sample appears. In the particular case of FIG. 7, the histogram 704 corresponds to sample 708.

As another example of the interactivity of display 700, a user can click, touch, or "mouse over" an icon or button and cause a color key to be displayed. An actual visual display like that shown in FIG. 7 would include color to highlight samples and to highlight portions of the histogram. Color might also be used for the distribution curve overlay pictured on histogram 704. For clarity of illustration in FIG. 7, varied shading or fill is used for illustrative purposes.

FIG. 8 is a graph illustrating the application of expectation-maximization to Gaussian mixture models according to some aspects. These Gaussian functions defined by using Gaussian mixture models can be used for the statistical analysis shown at block 508 of FIG. 5. Graph 800 shows a number of subpopulations, which are used as input for Gaussian mixture modeling to define Gaussian functions for each subpopulation. The Gaussian functions can be used to describe the statistical distribution of zircons in each sediment sample. In some aspects, the subpopulations are used as a priori constraints on an expectation-maximization (EM) algorithm to generate mixture models for each of the subpopulations. In FIG. 8, an expectation-maximization algorithm is run over three steps applied to Gaussian mixture models on predefined zircon subpopulations. The initial Gaussian function 802 is overlain on the histogram of the subpopulations. Through the EM algorithm-generation of Gaussian mixture models, the system uses machine learning to ascertain what it needs to know about the current sample in order to automatically produce one or more appropriate Gaussian functions to be evaluated in order to analyze the sample. Functions from EM maximization with various difference likelihoods are shown as lines 804. An actual visual display like that shown in FIG. 8 might include color to highlight portions of the histogram and to distinguish in EM maximization functions. For clarity of illustration in FIG. 7, varied shading or fill is provided for the histogram portion.

Figure 9A:
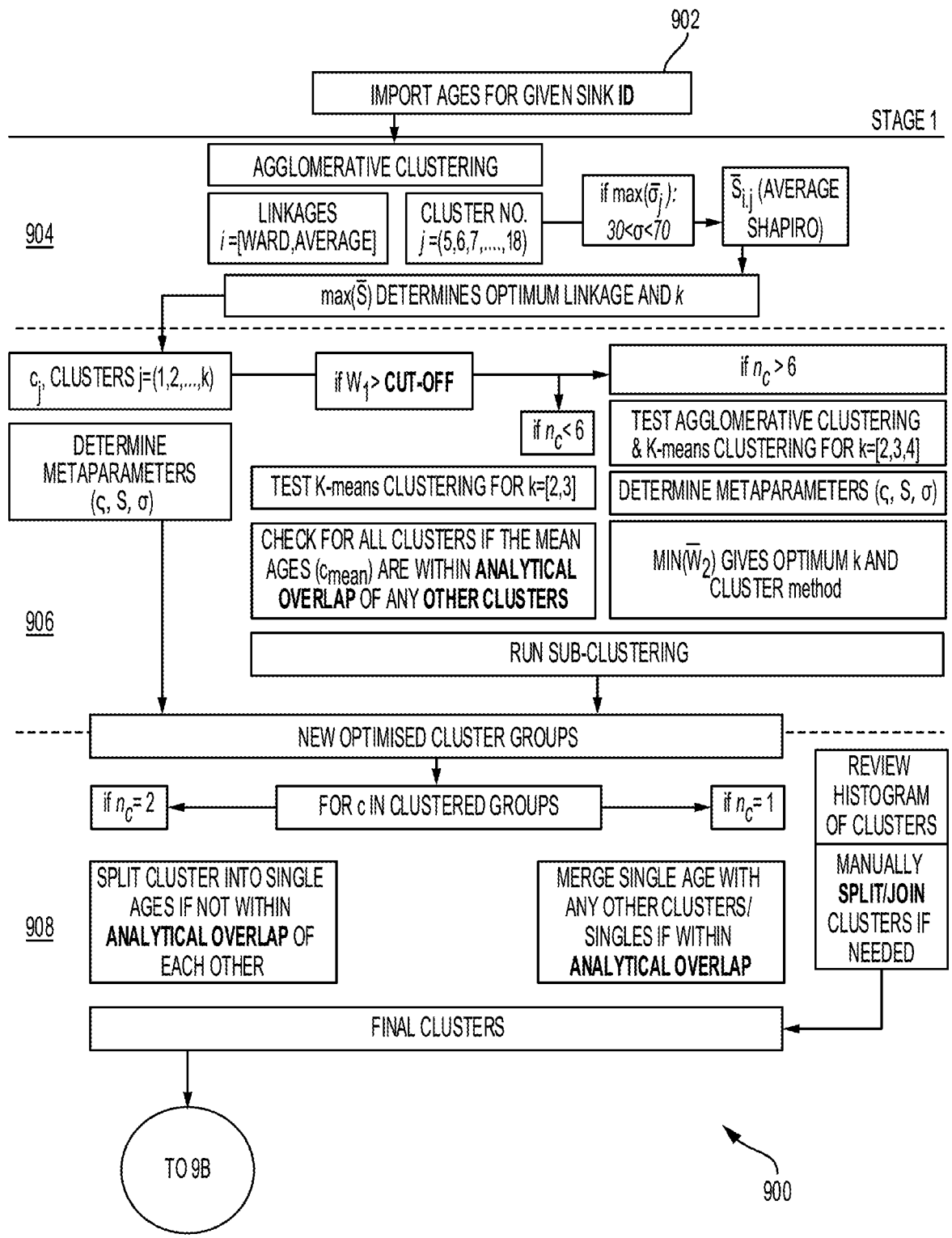
FIG. 9A and FIG. 9B depict a flowchart illustrating a process for provenance analysis and display according to some aspects. The flowchart is broken into two figures for clarity of illustration.
Figure 9B:
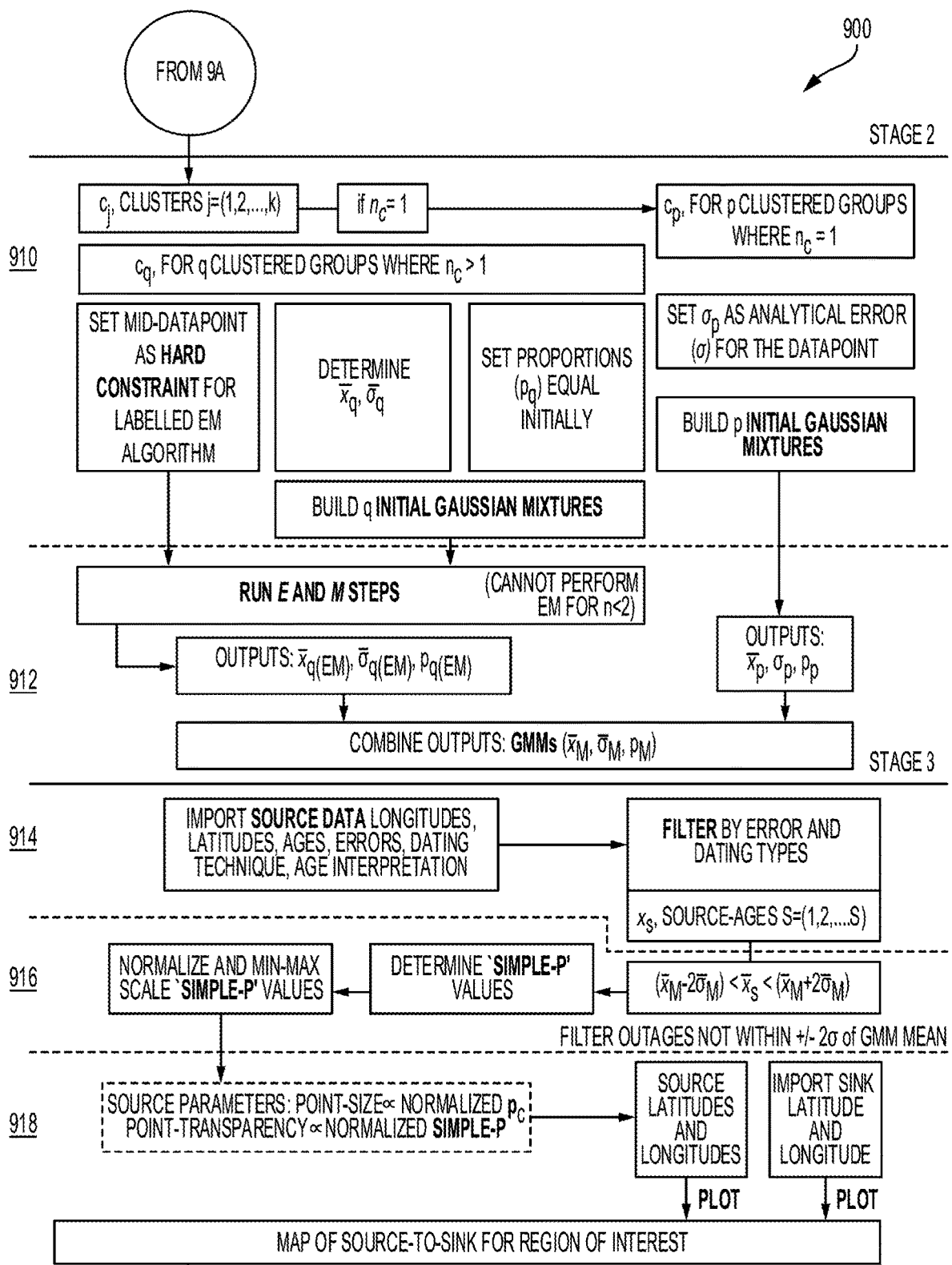

FIGS. 9A and 9B depict a flowchart illustrating a process 900 for provenance analysis and display according to some aspects. The flowchart is broken into two figures for clarity of illustration. The flowchart is further divided into three stages of processing and these stages are indicated with appropriate legends. Each stage is further divided into sections. Process 900 begins with block 902 of FIG. 9A, where detrital zircon ages for sediment samples provided in publicly available sources are extracted and imported. Agglomerative clustering as previously described with respect to FIGS. 1-3 and block 506 of FIG. 4 takes place in Stage 1 of process 900. Linkages based on Ward continuity i are used for each cluster c, number $j(c_j)$, where, $$\text{if max}(\overline{\sigma}_j): 30<\sigma<70$$

and a maximum average Shapiro score $\overline{S}$, the optimum linkage and k value for clustering, is determined in section 904. In section 906 of process 900, metaparameters for bandwidth density, Shapiro-Wilk-test, and standard deviation ($\varsigma$, S, $\sigma$) are determined for each cluster $c_j$ of the k clusters determined in section 904. The Shapiro-Wilk-test parameter gives an indication of the degree to which the population is normally distributed and the bandwidth density describes the density within a distribution. A high Shapiro-Wilk-test value indicates a statistically defined shape. A high bandwidth density indicates optimized clusters, such that data is grouped tightly. The metaparameters used to calculate $W_1$, a weighted sum of the metaparameters. If $W_1$, is greater than a cut-off value then a sub-clustering algorithm is run. Weightings and the cut-off value are empirically determined. Sub-clustering is achieved by trialing one or more clustering algorithms, for example agglomerative (average linkage) or K-means clustering on data from the initial cluster to define k=[2,3,4] sub-clusters. The optimum k value and cluster method are given by the minimum of the mean of the weighted sum of metaparameters for the sub-clusters:

$$\min(\overline{W}_2).$$

The average analytical error of each resulting sub-cluster is calculated and checked to ensure no sub-cluster is within error of any other.

At section 908 of Stage 1 of process 900, the analytical error on each of the zircon ages (data points n, where $n_{c(j)}$ is the number of data points, $\overline{x}_{c(j)}$ is the mean age, and $\overline{\sigma}_{c(j)}$ is the standard deviation for a given cluster) is taken into account and the processing device 102 joins clusters that are within analytical error of each other, setting $n_c$, the number of clusters, to a value of 2, and splits clusters that are outside of each other's analytical error, setting $n_c$, the number of clusters to a value of 1. In some aspects, a user can interactively review the clustering and manually split or join clusters as needed, while watching results being displayed.

Stage 2 of process 900, shown in FIG. 9B illustrates Gaussian mixture modeling as mentioned with respect to block 508 of FIG. 5. The subpopulations and clusters defined in Stage 1 are used to as an input to Gaussian mixture modelling so that machine learning can be employed to define Gaussian functions for each population which can be used to describe the statistical distribution of zircons in each sediment sample. The subpopulations defined in Stage 1 are used as a priori constraints on an expectation-maximization (EM) algorithm to generate mixture models for each of the subpopulations. In section 910, initial Gaussian mixture models p are built for clusters that were previously joined. $x_i$ is an individual sink data point and as is the corresponding age error. Outputs $\overline{X}_p, \sigma_p, p_p$ are provided, where $\sigma_p$ indicates the analytical error and $\overline{X}_p$ is mean age. Gaussian mixture models q are built with proportion values initially set to equal for clusters that were previously split. EM is run in section 912 for mixture models q only, since EM cannot be performed where n<2. EM produces outputs $\overline{X}_{q(EM)}, \sigma_{q(EM)}, p_{q(EM)}$. The output from the EM process and the outputs from Gaussian mixture models p are combined to produce Gaussian mixture models (GMMs) of $\overline{X}_M, \sigma_M, p_M$, where $\overline{X}_M$ is the mean of the Gaussian mixture component distribution, $\sigma_M$ is the standard deviation of the Gaussian mixture component distribution, $p_m$ represents the mixture weights as proportions the individual component M of the whole GMM, and the values of $x_s$ are each individual source-ages (data points).

Still referring to FIG. 9B, Stage 3 of process 900 compares the defined zircon subpopulations output from Stage 2 to an entire hinterland geochronology dataset in order to identify areas of likely sediment provenance for each of the zircon subpopulations in the sediment sample. To accomplish this, hinterland geochronology samples with large analytical error are removed from the dataset, each hinterland sample is compared with each zircon subpopulation, and a P score is calculated for each. The P score represents the probability that the detrital zircon subpopulation is from the same population as the hinterland sample, and simple-P values are used. In section 914 of FIG. 9B, source data including geolocation, ages, errors, dating techniques and age interpretations is imported and filtered by error and dating types. In section 916, ages not within +/−2σ of the Gaussian mixture model mean are filtered out as shown by:

$$(\overline{x}_M - 2\overline{\sigma}_M) < \overline{x}_s < (x + 2\sigma).$$

simple-P values are then determined, normalized, and placed on a min-max scale.

In section 918 of FIG. 9B, the calculated P scores are used to plot a map like that shown in FIG. 7, showing the detrital sample location and the location of all hinterland samples related to the zircon subpopulations. The map plotting and display optionally includes normalizing point size and transparency, and color values can be assigned. Source and sink longitudes and latitudes are imported and used to map the region of interest at block 920, which can also be stored as a paleographic map 114 of FIG. 1. The hinterland samples can be colored to represent each zircon subpopulation in the detrital sample, sized relative to the proportionality of their related zircon subpopulation as is visible in FIG. 7, and shading with transparency indicating their P score. Other methods for visually displaying the results can be used, as examples, heat maps and choropleths. The geospatial results are reconstructed on a geodynamic plate tectonic model to the age of deposition of the detrital sediment sample. This technique provides the user with a visualization of the paleogeography at the time of deposition and allows the user to discount sediment source areas that may not have been connected to the sink at the time of deposition. This display may highlight previously unknown sediment source areas that are no longer geographically connected to the sink in the present day.

The system of FIG. 1 can also conduct detrital geochronology sink-to-sink analysis. The detrital zircon age-distribution for a clastic sink sample can be used to describe its provenance signature. Comparisons of multiple age-distributions can therefore be useful for identifying dissimilarity amongst samples indicating changes to provenance and used to infer changes in sediment-routing systems. In petroleum exploration, understanding of sediment-routing systems can be used to project regions of high reservoir quality in sedimentary basins. A recent surge in the quantity of detrital zircon data available highlights the importance of efficient data analysis techniques in understanding provenance implications from large datasets.

Figure 10:
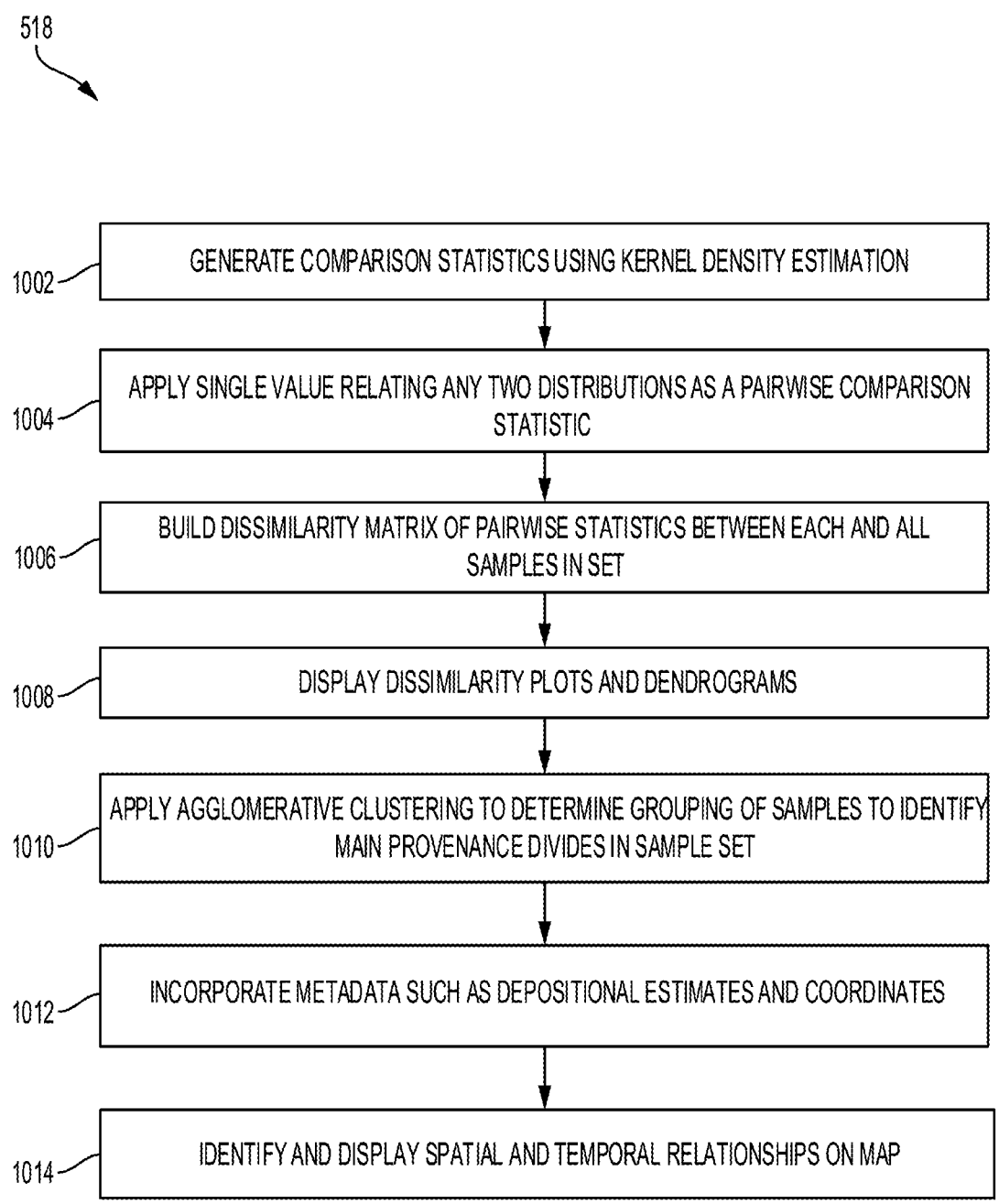
FIG. 10 is a flowchart illustrating a process for sink-to-sink analysis and display according to some aspects.

FIG. 10 is a flowchart illustrating a process for sink-to-sink analysis and display according to some aspects. Process 518 from FIG. 5 shown in detail in FIG. 10 automates multi-sample analysis techniques so they can be incorporated into the automated provenance investigation described herein to identifying spatio-temporal changes within the sedimentary system by assessing the levels of similarity between age-populations and to aid in understanding the controls on regional provenance. At block 1002 of process 518, processing device 102 generates comparison statistics using kernel density estimation to calculate dissimilarity values representing differences between sediment samples, such as the sediment sample being reviewed in FIG. 7 and additional sediment samples. At block 1004, a single value relating any two distributions as a pairwise comparison statistic is applied. A dissimilarity matrix is built of pairwise statistics between each and all samples in the set of samples under evaluation at block 1006. At block 1008, a dendrogram and age distributions can be displayed on display device 126.

Still referring to FIG. 10, at block 1010, agglomerative clustering can be performed by processing device 102 based on a user selection to determine the grouping of samples so that the main provenance divides in the sample set can be identified and metadata can be incorporated into the sample set at block 1012. Introducing agglomerative clustering to quantify levels of dissimilarity between samples that are indicative of changes in provenance signature effectively determines natural divides in the dataset. The dissimilarity values can be substituted for distance metrics, so that there is no requirement for using dimensionality-reducing algorithms, which can be unstable at low data volumes, and the dissimilarity values can also be represented in the dendrograms. The metadata (sample locations, geological formation, depositional age) are incorporated to automatically test for and identify spatial relationships, temporal relationships, or both in any given dataset. At block 1014 spatial and temporal relationships can then be displayed on either of the maps previously discussed, or any other appropriate displayed map.

Figure 11:
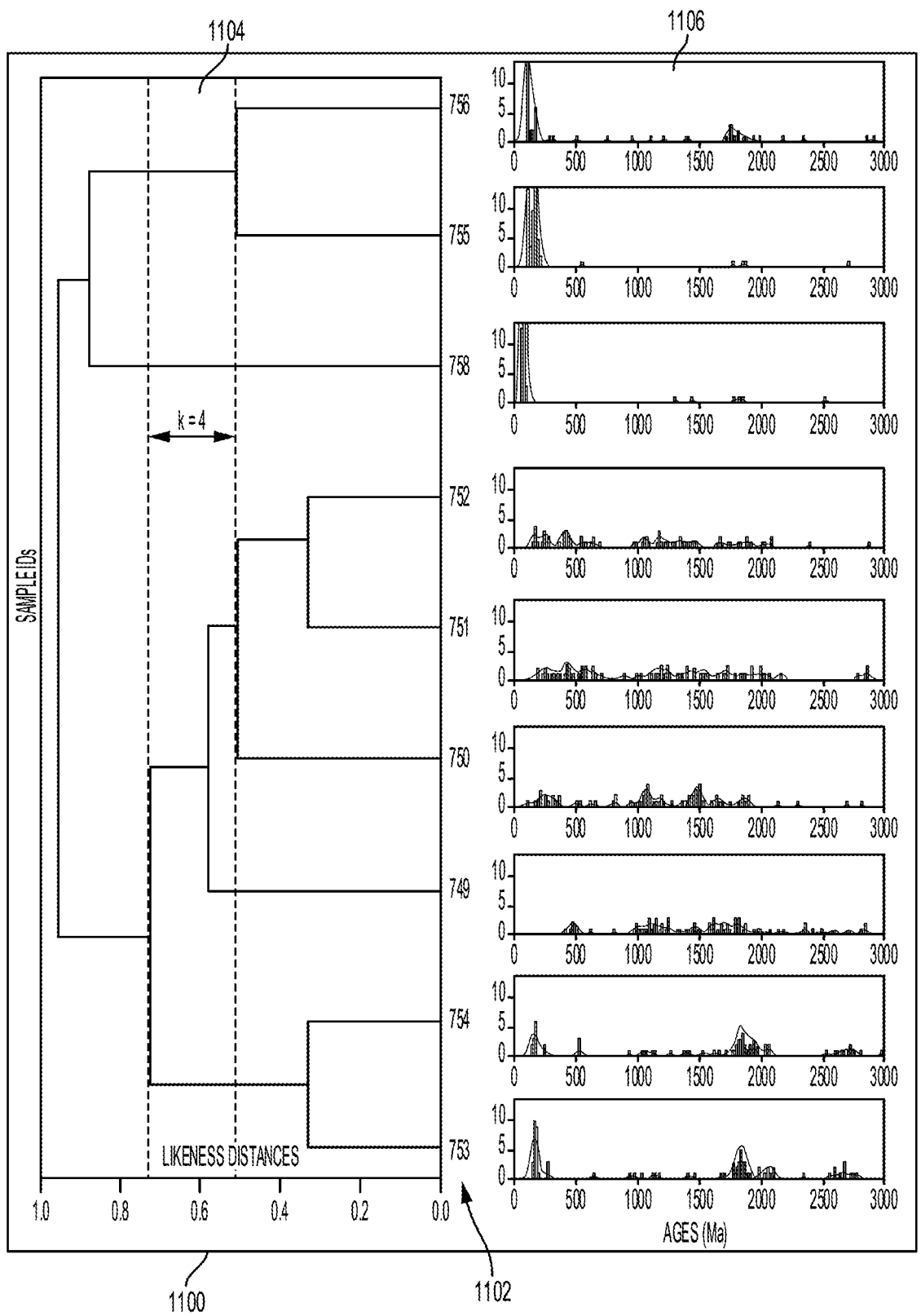
FIG. 11 depicts a graphical display including a dendrogram and age distributions according to some aspects.

FIG. 11 depicts a graphical display including a dendrogram and age distributions as described above according to some aspects. This display can be shown on display device 126 of FIG. 1. Sample identifiers are on the vertical axis. The column in the middle shows the numerical identifiers for various samples. Dendrogram 1104 indicates dissimilarity values by showing likeness distances. To indicate scale, the likeness distance when k=4 is shown. The right side of screen display 1100 illustrates age distributions with a histogram for each sample, such as histogram 1106.

In some aspects, a source-to-sink analysis and display system is provided according to one or more of the following examples. As used below, any reference to a series of examples is to be understood as a reference to each of those examples disjunctively (e.g., "Examples 1-4" is to be understood as "Examples 1, 2, 3, or 4").

Example #1: A computing device includes a processing device and a non-transitory memory device. The non-transitory memory device includes instructions that are executable by the processing device to cause the processing device to perform operations including grouping target geochronological data and reference geochronological data into distinct population groups representing a reference population and target populations, characterizing subpopulations within the reference population and the target populations according to at least one statistical attribute, comparing the subpopulations within the reference population and the target populations based on the at least one statistical attribute to determine correlations between the reference population and the target populations, and concurrently displaying the correlations relative to a present day geographic map with links between source regions and sink regions, and displaying the correlations relative to a paleogeographic map as of a time of relevance.

Example #2: The computing device of example 1 wherein the paleographic map is based at least in part on a geodynamic plate tectonic model.

Example #3: The computing device of example(s) 1-2 wherein the operations further include defining the subpopulations using agglomerative clustering of zircon age data.

Example #4: The computing device of example(s) 1-3 wherein the operations further include receiving input including geological rule values and defining sub-clusters within the subpopulations using the geological rule values.

Example #5: The computing device of example(s) 1-4 wherein the operations further include displaying the subpopulations according to geological age.

Example #6: The computing device of example(s) 1-5 wherein the subpopulations are displayed as a histogram of geological age versus frequency.

Example #7: The computing device of example(s) 1-6 wherein the at least one statistical attribute further includes at least one of a mean, a variance, or a proportion of total population.

Example #8: A method includes grouping, by a processing device, target geochronological data and reference geochronological data into distinct population groups representing a reference population and target populations, characterizing, by the processing device, subpopulations within the reference population and the target populations according to at least one statistical attribute, comparing, by the processing device, the subpopulations within the reference population and the target populations based on the at least one statistical attribute to determine correlations between the reference population and the target populations, and concurrently, on a display device, displaying the correlations relative to a present day geographic map with links between source regions and sink regions, and displaying the correlations relative to a paleogeographic map as of a time of relevance.

Example #9: The method of example 8 wherein the paleographic map is based at least in part on a geodynamic plate tectonic model.

Example #10: The method of example(s) 8-9 further includes defining the subpopulations using agglomerative clustering of zircon age data.

Example #11: The method of example(s) 8-10 further includes receiving input including geological rule values and defining sub-clusters within the subpopulations using the geological rule values.

Example #12: The method of example(s) 8-11 further includes displaying the subpopulations according to geological age.

Example 13 #: The method of example(s) 8-12 wherein the at least one statistical attribute further includes at least one of mean, variance, or proportion of total population and the method further includes storing the at least one statistical attribute.

Example #14: The method of example(s) 8-13 wherein the subpopulations are displayed as a histogram of geological age versus frequency.

Example #15: A non-transitory computer-readable medium that includes instructions that are executable by a processing device for causing the processing device to perform the method of any of example(s) 8-14.

The foregoing description of the examples, including illustrated examples, has been presented only for the purpose of illustration and description and is not intended to be exhaustive or to limit the subject matter to the precise forms disclosed. Numerous modifications, combinations, adaptations, uses, and installations thereof can be apparent to those skilled in the art without departing from the scope of this disclosure. The illustrative examples described above are given to introduce the reader to the general subject matter discussed here and are not intended to limit the scope of the disclosed concepts.

What is claimed is:

1. A computing device comprising:
   a processing device; and
   a non-transitory memory device comprising instructions that are executable by the processing device to cause the processing device to perform operations comprising:
      grouping target geochronological data and reference geochronological data into distinct population groups representing a reference population and target populations;
      characterizing, using a clustering operation, subpopulations within the reference population and the target populations according to at least one statistical attribute;
      comparing the subpopulations within the reference population and the target populations based on the at least one statistical attribute to determine correlations between the reference population and the target populations; and
      concurrently displaying the correlations relative to a present day geographic map with links between source regions and sink regions, and displaying the correlations relative to a paleogeographic map as of a time of relevance.

2. The computing device of claim 1 wherein the paleogeographic map is based at least in part on a geodynamic plate tectonic model.

3. The computing device of claim 1 wherein the clustering operation comprises defining the subpopulations using agglomerative clustering of zircon age data.

4. The computing device of claim 3 wherein the operations further comprise:
   receiving input including geological rule values; and
   defining sub-clusters within the subpopulations using the geological rule values.

5. The computing device of claim 1 wherein the operations further comprise displaying the subpopulations according to geological age.

6. The computing device of claim 5 wherein the subpopulations are displayed as a histogram of geological age versus frequency.

7. The computing device of claim 1 wherein the at least one statistical attribute further comprises at least one of a mean, a variance, or a proportion of total population.

8. A method comprising:
   grouping, by a processing device, target geochronological data and reference geochronological data into distinct population groups representing a reference population and target populations;
   characterizing, by the processing device, subpopulations within the reference population and the target populations according to at least one statistical attribute using a clustering operation;
   comparing, by the processing device, the subpopulations within the reference population and the target populations based on the at least one statistical attribute to determine correlations between the reference population and the target populations; and
   concurrently, on a display device, displaying the correlations relative to a present day geographic map with links between source regions and sink regions, and displaying the correlations relative to a paleogeographic map as of a time of relevance.

9. The method of claim 8 wherein the paleogeographic map is based at least in part on a geodynamic plate tectonic model.

10. The method of claim 8 wherein the clustering operation comprises agglomerative clustering of zircon age data.

11. The method of claim 10 further comprising:
    receiving input including geological rule values; and
    defining sub-clusters within the subpopulations using the geological rule values.

12. The method of claim 8 further comprising displaying the subpopulations according to geological age.

13. The method of claim 8 wherein the at least one statistical attribute further comprises at least one of mean, variance, or proportion of total population and the method further comprises storing the at least one statistical attribute.

14. A non-transitory computer-readable medium that includes instructions that are executable by a processing device for causing the processing device to perform operations to display source-to-sink analysis information, the operations comprising:
    grouping target geochronological data and reference geochronological data into distinct population groups representing a reference population and target populations;
    characterizing subpopulations within the reference population and the target populations according to at least one statistical attribute using a clustering operation;
    comparing the subpopulations within the reference population and the target populations based on the at least one statistical attribute to determine correlations between the reference population and the target populations; and
    concurrently, on a display device, displaying the correlations relative to a present day geographic map with links between source regions and sink regions, and displaying the correlations relative to a paleogeographic map at a time of relevance.

15. The non-transitory computer-readable medium of claim 14 wherein the paleogeographic map is based at least in part on a geodynamic plate tectonic model.

16. The non-transitory computer-readable medium of claim 14 wherein the clustering operation comprises defining the subpopulations using agglomerative clustering of zircon age data.

17. The non-transitory computer-readable medium of claim 16 wherein the operations further comprise:
    receiving input including geological rule values; and defining sub-clusters within the subpopulations using the geological rule values.

18. The non-transitory computer-readable medium of claim 14 wherein the operations further comprise displaying the subpopulations according to geological age.

19. The non-transitory computer-readable medium of claim 18 wherein the subpopulations are displayed as a histogram of geological age versus frequency.

20. The non-transitory computer-readable medium of claim 14 wherein the at least one statistical attribute comprises at least one of mean, variance, or proportion of total population and the operations further comprise storing the at least one statistical attribute.

\* \* \* \* \*